(12) United States Patent
Tung et al.

(10) Patent No.: US 8,993,342 B2
(45) Date of Patent: Mar. 31, 2015

(54) MAGNETIC SEPARATION UNIT, MAGNETIC SEPARATION DEVICE AND METHOD FOR SEPARATING MAGNETIC SUBSTANCE IN BIO-SAMPLES

(75) Inventors: Mean-Jue Tung, Kinmen County (TW); Yu-Ting Huang, Hsinchu County (TW); Li-Kou Chen, Hsinchu (TW); Yi-Shan Lin, Taipei (TW); Hsiang-Ming Huang, Taipei (TW); Shinn-Zong Lin, Taichung (TW); Woei-Cherng Shyu, Taipei (TW); Hsiao-Jung Wang, Hualien County (TW)

(73) Assignee: Industrial Technology Research Institute, Hsinchu (TW)

( * ) Notice: Subject to any disclaimer, the term of this patent is extended or adjusted under 35 U.S.C. 154(b) by 925 days.

(21) Appl. No.: 13/159,361

(22) Filed: Jun. 13, 2011

(65) Prior Publication Data

US 2012/0255913 A1 Oct. 11, 2012

(30) Foreign Application Priority Data

Apr. 11, 2011 (TW) .............................. 100112412 A

(51) Int. Cl.
*B03C 1/00* (2006.01)
*G01N 1/34* (2006.01)
*B03C 1/28* (2006.01)
(Continued)

(52) U.S. Cl.
CPC ............. *B03C 1/288* (2013.01); *Y10T 436/255* (2013.01); *Y10T 436/25375* (2013.01); *G01N 33/0098* (2013.01); *Y10T 436/25* (2013.01); *B03C 1/0332* (2013.01); *B03C 2201/18* (2013.01); *B03C 2201/26* (2013.01)

USPC ......................................................... 436/177

(58) Field of Classification Search
CPC .. B03C 1/0332; B03C 1/288; B03C 2201/26; B03C 2201/28; B03C 2201/18; B03C 2201/20; G01N 33/0098; Y10T 436/255; Y10T 436/25; Y10T 436/25375
See application file for complete search history.

(56) References Cited

U.S. PATENT DOCUMENTS

| 5,411,863 | A | 5/1995 | Miltenyi |
| 5,711,871 | A | 1/1998 | Miltenyi |
| 6,417,011 | B1 | 7/2002 | Miltenyi |

(Continued)

FOREIGN PATENT DOCUMENTS

| CN | 2609931 Y | 4/2004 |
| EP | 0941766 A2 | 9/1999 |

(Continued)

OTHER PUBLICATIONS

Tibbe, Arjan G. J. et al. "Magnetic field design for selecting and aligning immunomagnetic labeled cells." Cytometry (2002) 47 163-172.*

(Continued)

*Primary Examiner* — Christopher A Hixson

(57) ABSTRACT

A magnetic separation unit is provided, including a first member made of non-magnetic materials comprising a trench extending within the first member and a second member made of magnetic materials including a protrusion portion protruding over a surface of the second member, wherein the first member connects the second member such that the trench functions as a fluid channel formed between the first and second members, and the protrusion portion of the second member is contained by the trench of the first member.

23 Claims, 21 Drawing Sheets

(51) Int. Cl.
*B03C 1/033* (2006.01)
*G01N 33/00* (2006.01)

(56) References Cited

U.S. PATENT DOCUMENTS

| | | |
|---|---|---|
| 2004/0018611 A1 | 1/2004 | Ward et al. |
| 2004/0108253 A1 | 6/2004 | Broyer et al. |
| 2008/0131949 A1* | 6/2008 | Bortolin et al. ............ 435/173.9 |
| 2009/0152176 A1 | 6/2009 | Kipp et al. |
| 2011/0147278 A1 | 6/2011 | Tung et al. |

FOREIGN PATENT DOCUMENTS

| | | |
|---|---|---|
| EP | 1308211 A2 | 5/2003 |
| TW | 201121655 | 7/2011 |
| WO | WO 99/19071 | 4/1999 |
| WO | WO 2009/117611 A2 | 9/2009 |

OTHER PUBLICATIONS

Andreas Radbruch et al., "High-Gradient Magnetic Cell Sorting", Methods in Cell Biology, 1994, pp. 387-pp. 403, vol. 42, Academic Press, Inc.

Taiwan Patent Office, Office Action, Patent Application Serial No. 100112412, Mar. 25, 2013, Taiwan.

Haitao Chen et al., "2D Modeling and Preliminary in Vitro Investigation of a Prototype High Gradient Magnetic Separator for Biomedical Applications," Medical Engineering Physics, 2008, pp. 1-8, vol. 30, Elsevier Ltd., US.

Stefan Miltenyi et al., " High Gradient Magnetic Cell Separation with MACS[1]," Cytometry, 1990, pp. 231-238, vol. 11, Wiley-Liss, Inc., US.

\* cited by examiner

MAGNETIC SEPARATION UNIT, MAGNETIC SEPARATION DEVICE AND METHOD FOR SEPARATING MAGNETIC SUBSTANCE IN BIO-SAMPLES

CROSS REFERENCE TO RELATED APPLICATIONS

This Application claims priority of Taiwan Patent Application No. 100112412, filed on Apr. 11, 2011, the entirety of which is incorporated by reference herein.

BACKGROUND

1. Technical Field

The disclosure relates to bio-separation devices, and in particular, to magnetic separation units and magnetic separation devices capable of separating magnetic substances in bio-samples and methods for separating the magnetic substances in the bio-samples.

2. Description of the Related Art

In the field of biology, many efficient techniques for separating one type of cell or a class of cells from a complex cell suspension are disclosed and have wide applications. The ability to remove certain cells from a clinical blood sample that are indicative of a particular disease state could be useful as a diagnostic tool for better understanding the particular state of the disease.

It has been shown that cells tagged with micron sized (>1 µm) magnetic or magnetized particles can be successfully removed or separated from mixtures by using magnetic devices. For the removal of the desired cells, i.e., cells which provide valuable information, a desired cell population is magnetized and removed from a complex liquid mixture (so-called positive selection or positive separation). In an alternative method, the undesirable cells, i.e., cells that may prevent or alter the results of a particular procedure are magnetized and subsequently removed with a magnetic device (so-called negative selection or negative separation).

Cell separation methods utilizing magnetic tags are mainly divided into two kinds, wherein one kind is the so-called column-based separation method which uses magnetic particles with a smaller size or a weaker magnetic magnetization as tags, and separates these tags in a column filled with magnetic fillers. High magnetic gradients are generated close to the surfaces of the magnetic fillers when a magnetic field is applied to the column. The other kind is the so-called tube-based separation method using a centrifugal tube as a separation vessel. The magnetic tags are separated within a centrifugal tube by magnetic field generated by a magnet outside the tube. Therefore, larger sized tags or stronger magnetic magnetization are needed for separation efficiency. Note that for the tube-based separation method there is no need to use a column with magnetic fillers, like the column-based separation method.

However, separation efficiency of the magnetic cells depends on the magnetic forces acting on the magnetic tags. Thus, an increase in the magnetic field or magnetic field gradient improves separation efficiency. However, whether using permanent magnets or electromagnets, the magnetic field and magnetic field gradient decrease as the distance increases. Therefore, separation efficiency of the magnetic cells in conventional centrifugal tubes is difficult to improve, because high magnetic filed and high magnetic field gradient cannot be applied to magnetic materials in the conventional tubes.

SUMMARY

Accordingly, a magnetic separation unit comprising a member made of a magnetic material is provided such that a high magnetic field gradient of an external magnetic field can be extended into the magnetic separation unit to improve magnetic separation efficiency. In addition, a magnetic separation device using the magnetic separation unit and a method for separating magnetic substances in a bio-sample are also provided.

An exemplary magnetic separation unit comprises a first member made of non-magnetic materials comprising a trench extending within the first member and a second member made of magnetic materials comprising a protrusion portion protruding over a surface of the second member, wherein the first member connects to the second member such that the trench functions as a fluid channel formed between the first and second members, and the protrusion portion of the second member is contained by the trench of the first member.

An exemplary magnetic separation device comprises a first magnetic field unit and the magnetic separation unit described previously. In one embodiment, the first magnetic field unit comprises a first magnetic yoke having opposite first and second surfaces and a plurality of first magnets respectively disposed over the first and second surfaces, wherein the same magnetic poles of the plurality of first magnets face the first magnetic yoke, and the magnetic separation unit described previously is disposed at one side of the first magnetic field unit, and wherein the second member of the magnetic separation unit is adjacent to the first magnetic field unit.

An exemplary method for separating magnetic substances in a bio-sample comprises: providing the magnetic separation device describe previously; providing a bio-sample solution, wherein the bio-sample solution comprises magnetic bio-substances or bio-substances labeled by a magnetic target; pumping the bio-sample solution through the fluid channel in the magnetic separation device, thereby attracting or repelling the magnetic bio-substances or bio-substances labeled by a magnetic target toward a sidewall of the magnetic separation unit adjacent and parallel to the first magnetic yoke; separating the first magnetic field unit from the magnetic separation unit; and providing a buffer solution and pumping the buffer solution through the fluid channel of the magnetic separation unit, thereby eluting the magnetic bio-substances or bio-substances labeled by magnetic targets left on the sidewall of the magnetic separation unit.

A detailed description is given in the following embodiments with reference to the accompanying drawings.

BRIEF DESCRIPTION OF THE DRAWINGS

The disclosure can be more fully understood by reading the subsequent detailed description and examples with references made to the accompanying drawings, wherein.

DETAILED DESCRIPTION OF THE DISCLOSURE

The following description is of the best-contemplated mode of carrying out the disclosure. This description is made for the purpose of illustrating the general principles of the disclosure and should not be taken in a limiting sense. The scope of the disclosure is best determined by reference to the appended claims.

Figure 1:
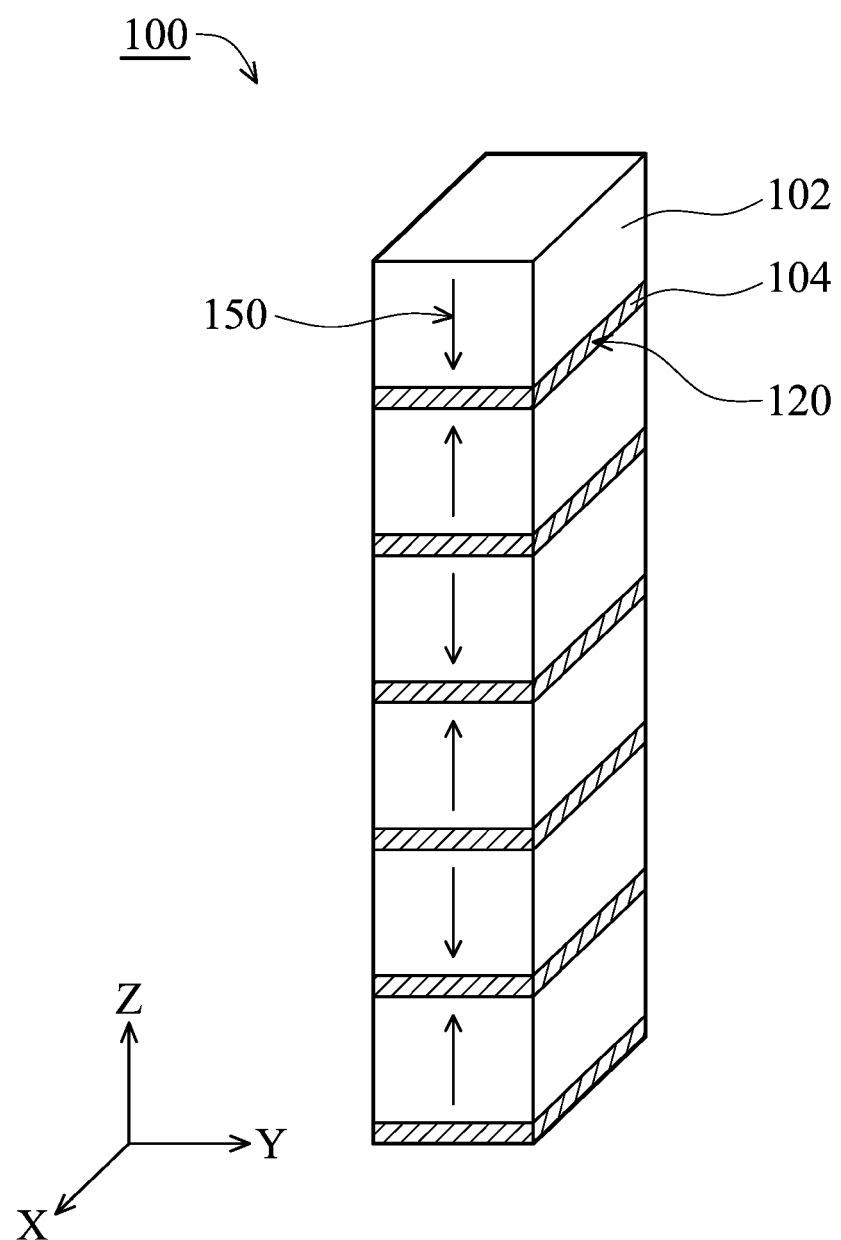
FIG. 1 is a schematic diagram showing a magnetic field unit according to an embodiment of the disclosure.
Figure 2:
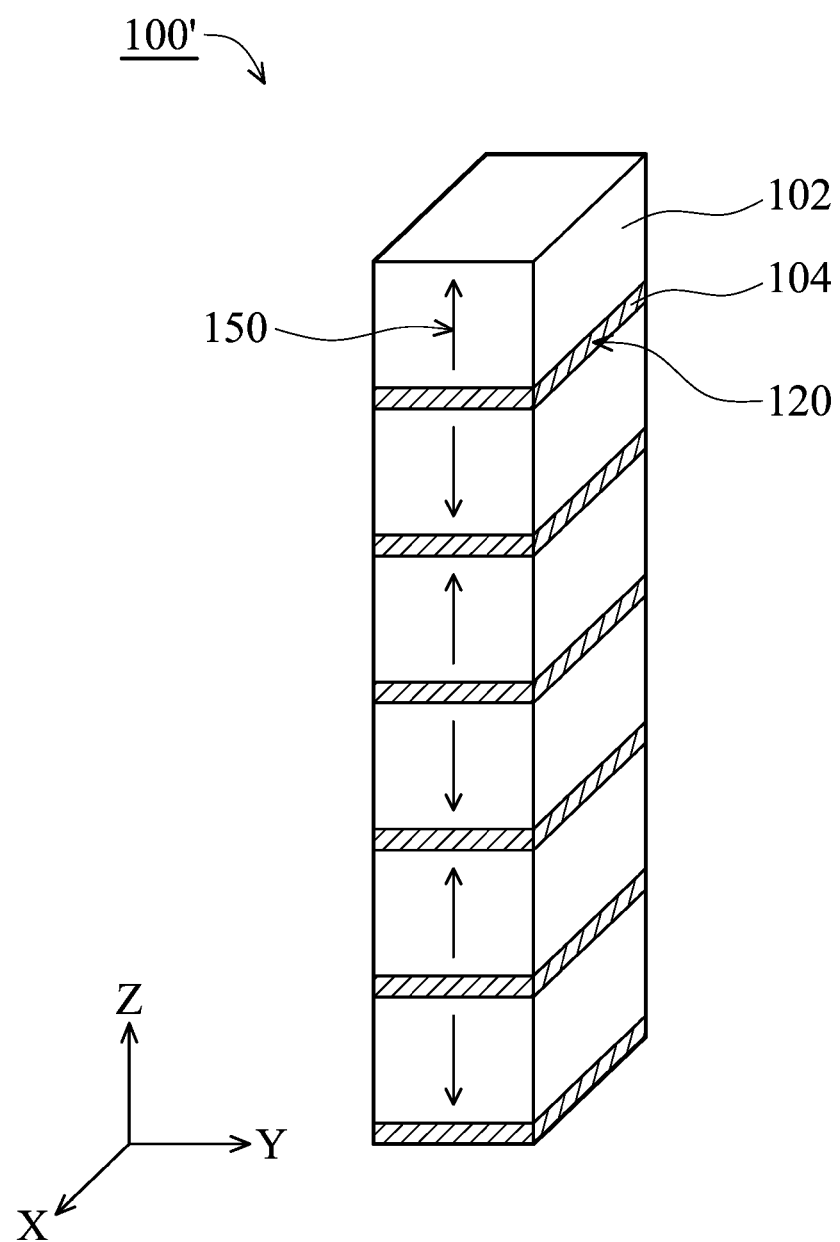
FIG. 2 is a schematic diagram showing a magnetic field unit according to another embodiment of the disclosure.

Magnetic separation devices according to various embodiments of the disclosure are illustrated in FIGS. 10-15 and details thereof are discussed in the following paragraphs, wherein each of the magnetic separation devices comprises at least one magnetic field unit and at least one magnetic separation unit. FIGS. 1-2 are schematic diagrams respectively showing a magnetic field unit utilized in the magnetic separation devices illustrated in FIGS. 10-15, and FIGS. 3-9 are schematic diagrams respectively showing a magnetic separation unit utilized in the magnetic separation devices illustrated in FIGS. 10-15.

As shown in FIGS. 1-2, magnetic field units according to various embodiments of the disclosure are illustrated. FIG. 1 illustrates a perspective diagram of an exemplary magnetic field unit 100, comprising a plurality of magnets 102 and a magnetic yoke 104 respectively interposed between the magnets 102. In this embodiment, the magnets 102 are illustrated as a rectangular pillar and the magnetic yoke 104 is illustrated as a rectangular plate. As shown in FIG. 1, two of the magnets 102 in the magnetic field unit 100 are disposed on opposite surfaces of the magnetic yoke 104, and the same magnetic pole of the two magnets 102 face the magnetic yoke 104. Herein, the arrow 150 represents the interior magnetic field direction from a south pole toward a north pole of each of the magnets 102.

In the magnetic field unit 100, as shown in FIG. 1, the magnets 102 and the magnetic yokes 104 are formed with similar shapes and similar surface areas, and the magnetic field unit 100 is illustrated as a rectangular pillar having a plurality of planar sidewall surfaces. Herein, the magnets 102 are formed with a surface area $A_m$ in contact with the magnetic yoke 104, and a sidewall surface 120 of each of the magnetic yokes 104 not in contact with the magnets 102 is formed with a surface area $A_y$. Due to the continuity of the magnetic flux lines, a magnetic flux density B at the sidewall surface 120 of the magnetic yoke 104 not in contact with the magnets 102 may be defined as follows:

$$B = 2B_d A_m / A_y \quad (1),$$

wherein $B_d$ represents a working magnetic flux density of the magnets 102. $B_d$ is typically affected by factors such as the shape of the magnets and demagnetization fields, and theoretically having a value which is less than that of the remanent flux density (Br) of the magnets 102. Adequately selected $A_m$ and $A_y$ may provide a strong magnetic field which may be greater than the remanent flux density (Br) of the magnets 102 at each of the sidewall surfaces 120 of the magnetic yoke 104 not in contact with the magnets 102, such that the magnetic field can be used in a process for separating magnetic substances in bio-samples. Herein, due to the arrangement of the plurality of magnetic yokes 104, a plurality of areas having strong magnetic fields capable of separating magnetic substances in bio-samples are provided in the magnetic field unit 100.

FIG. 2 illustrates a perspective diagram of another exemplary magnetic field unit 100' similar to the magnetic field unit 100 illustrated in FIG. 1. Herein, the same references represent the same components, and only differences between the magnetic field units 100 and 100' are discussed in the following.

As shown in FIG. 2, the magnetic field unit 100' is also formed with a plurality of magnets 102 and a plurality of magnetic yokes 104 respectively disposed between the magnets 102, wherein the directions of the interior magnetic fields (represented as arrow 150) in the magnets 102 in the magnetic field unit 100' are opposite to that of the magnets 102 located at the same places in the magnetic field unit 100 in FIG. 1. As to the arrangement shown in FIG. 2, a strong magnetic field can be thus formed near a sidewall surface 120 of each of the magnetic yokes 104 in the magnetic field unit 100', and the magnetic field unit 100' thus has a plurality of areas of strong magnetic fields which are greater than the remanent flux density (Br) of the magnets 102.

The magnets 102 used in the magnetic field units 100 and 100' illustrated in FIGS. 1-2 can be formed of materials such as NdFeB, SmCo, SmFeN, AlNiCo, ferrite, or combinations thereof. The magnets 102 can be formed in a configuration other than the rectangular pillar, such as circular pillar, triangular pillar or other polygonal pillar. In addition, the magnetic yokes 104 used in the magnetic field units 100 and 100' illustrated in FIGS. 1-2 can be formed of materials such as pure iron, magnetic stainless steel or metal soft magnetic materials having predetermined permeability. The metal soft magnetic materials having predetermined permeability can be, for example, iron, silicon steel, NiFe, CoFe, stainless steel, soft magnetic ferrites, or combinations thereof. In one embodiment, the magnets 102 used in the magnetic field units 100 and 100' can be provided with a thickness greater than 1 mm for easy application, but is not limited thereto, and the magnetic yokes 104 can be provided with a thickness of about 0.5-10 mm. In addition, for the purpose of fabricating components, a non-magnetic frame (not shown) made of materials such as stainless steel or aluminum alloys can be further provided to cover the magnetic field units 100 and 100' shown in FIGS. 1-2 from the outside. The non-magnetic frame can be also provided with an opening or a slot at a place near each of the magnetic yokes 104 used in the magnetic field units 100 and 100' to expose sidewall surfaces 120 of the magnetic yokes 104.

FIGS. 3-9 are schematic diagrams showing magnetic separation units used in the magnetic separation device according to various embodiments of the disclosure.

Figure 3:
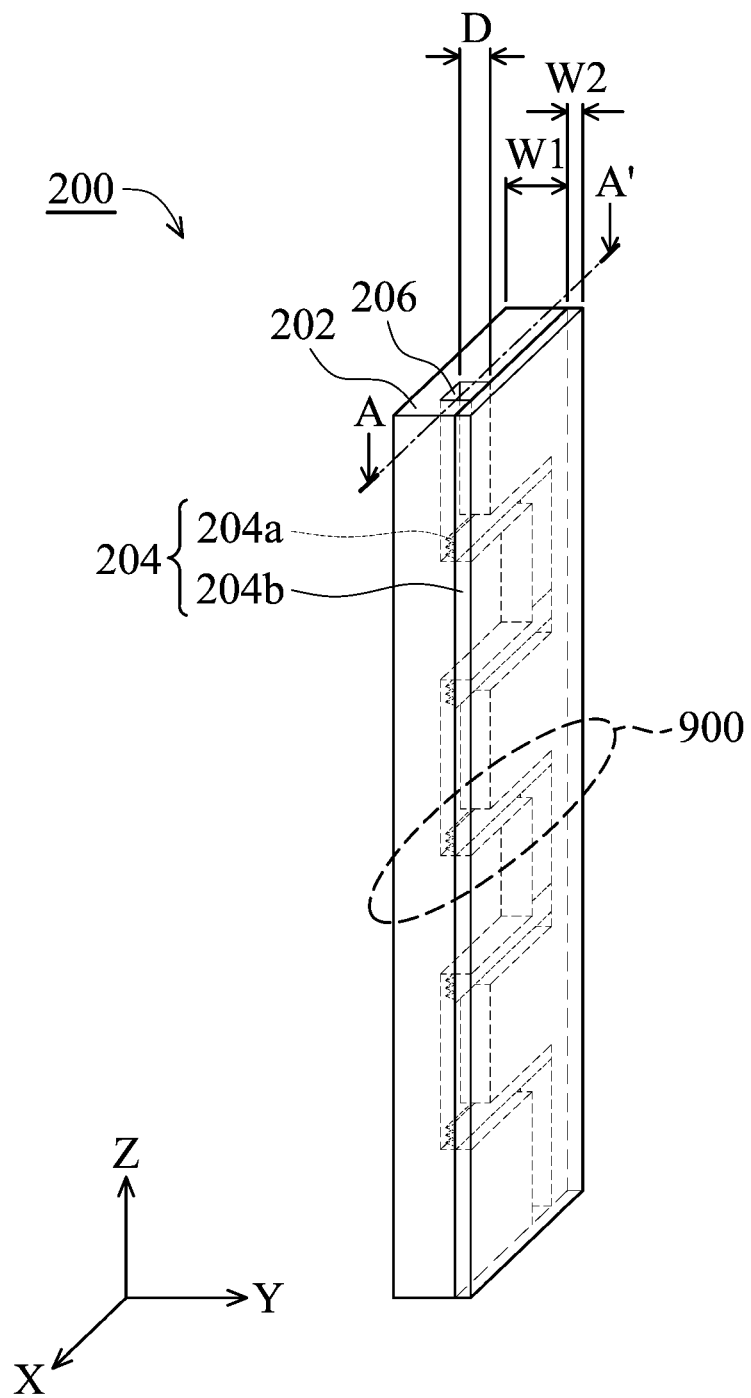
FIG. 3 is a schematic diagram showing a magnetic separation unit according to an embodiment of the disclosure.

FIG. 3 illustrates a perspective diagram of an exemplary magnetic separation unit 200, including a first member 202 made of non-magnetic materials and a second member 204 made of magnetic materials. A trench 206 is disposed at a surface of the first member 202 and the second member 204 comprises a planar portion 204b and a plurality of protrusion portions 204a. The trench 206 extends through the first member 202 from a top toward a bottom of the first member 202 and contains the plurality of protrusion portions 204a toward a fluid channel in the magnetic separation unit 200 after the first member 202 and the second member 204 are combined. Thus, in the magnetic separation process, a bio-sample solution can be pumped through the fluid channel of the magnetic separation unit 200 from a top to a bottom thereof.

As shown in FIG. 3, the first member 202 of the magnetic separation unit 200 is formed with a thickness W1 and the second member 204 of the magnetic separation unit 200 is formed with a thickness W2, and the trench 206 of the first member 202 is formed with a depth D. Herein, the first member 202 and the second member 204 are illustrated in a plate configuration and a width thereof can be adjusted according to a width of the corresponding magnetic field unit. In addition, locations of the first member 202 and the second member 204 shown in FIG. 3 can be exchanged and the trench 206 disposed at a surface of the first member 202 will be adjacent to the second member 204 and covered by the second member 204. Moreover, shapes and configurations of the first member 202 and the second member 204 are not limited by that shown in FIG. 3, and can be modified according corresponding configurations of the magnetic field unit 100 or 100'. In one embodiment, the second member 204 of the magnetic separation unit 200 may have a thickness W2 of about 0.02-1 mm.

Figure 4A:
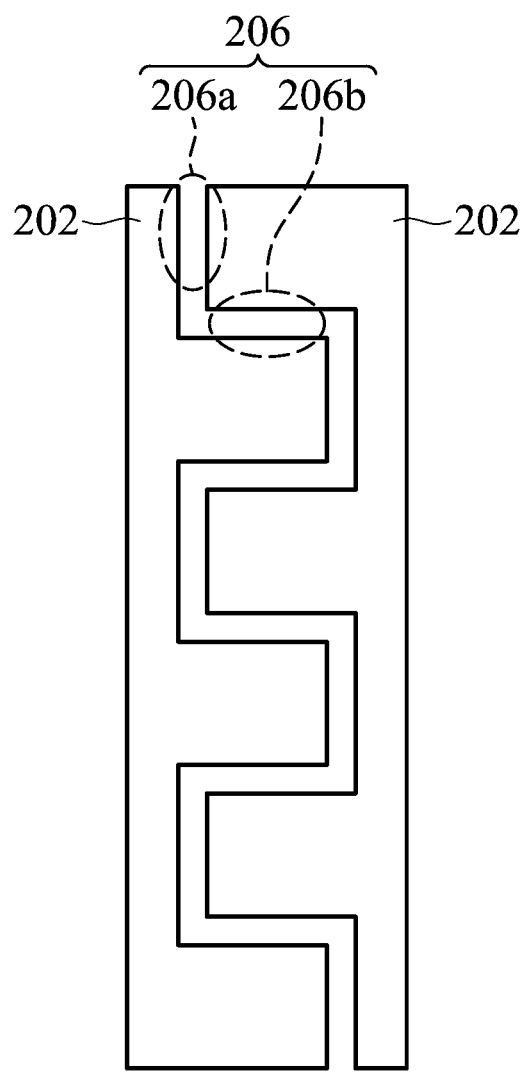
FIGS. 4a, 4b, 4c, 5a, 5b, 5c, 6a, 6b, 6c are schematic diagrams respectively showing a cross sectional view of a first member of the magnetic separation unit shown in FIG. 3 along a line A-A' according to various embodiments of the disclosure.

FIG. 4a illustrates an exemplary cross section of the magnetic separation unit 200 taken along a line A-A' in FIG. 3. Herein, the trench 206 of the first member 202 comprises a plurality of first sections 206a and a plurality of second sections 206b arranged in order, thereby forming the fluid channel passing through the first member 202 from a top toward a bottom of the first member 202. The first sections 206a and the second sections 206b are substantially perpendicular to each other. Herein, the first sections 206a are illustrated as portions of the trench which are perpendicular to a shorter side of the first member 202, and the second sections 206b are illustrated as portions of the trench 206 which are parallel to a shorter side of the first member 202, and the topmost one of the first sections 206a may function as an input end for receiving a bio-sample solution, and the bottommost one of the first sections 206a may function as an output end for exhausting the bio-sample solution.

Figure 5A:
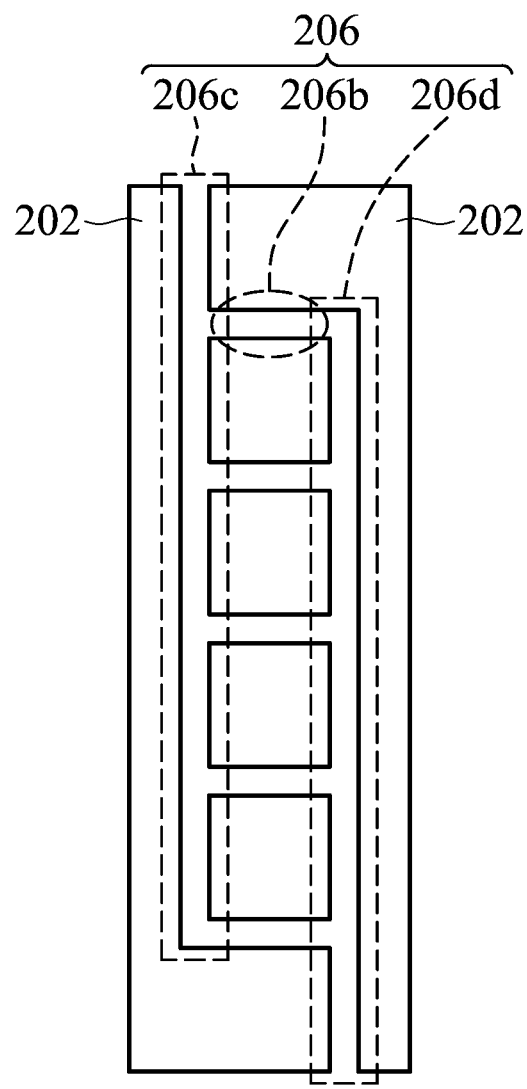

FIG. 5a illustrates another exemplary cross section of the magnetic separation unit 200 taken along a line A-A' in FIG. 3. Herein, the trench 206 of the first member 202 comprises a separated third section 206c and fourth section 206d, and a plurality of second sections 206b is simultaneously disposed and connected between the third section 206c and the fourth section 206d, thereby forming the fluid channel passing through the first member 202 from a top toward a bottom thereof. The third section 206c and the fourth section 206d are substantially perpendicular to the second sections 206b. Herein, the third section 206c and the fourth section 206d are illustrated as portions of the trench which are perpendicular to a shorter side of the first member 202, wherein the third section 206c is disposed at a top portion of the first member 202 to function as an input end for receiving a bio-sample solution, and the fourth section 206d is disposed at a bottom portion of the first member 202 to function as an output end for exhausting the bio-sample solution, and the second sections 206b are illustrated as portions of the trench which are parallel to a shorter side of the first member 202.

Figure 6A:
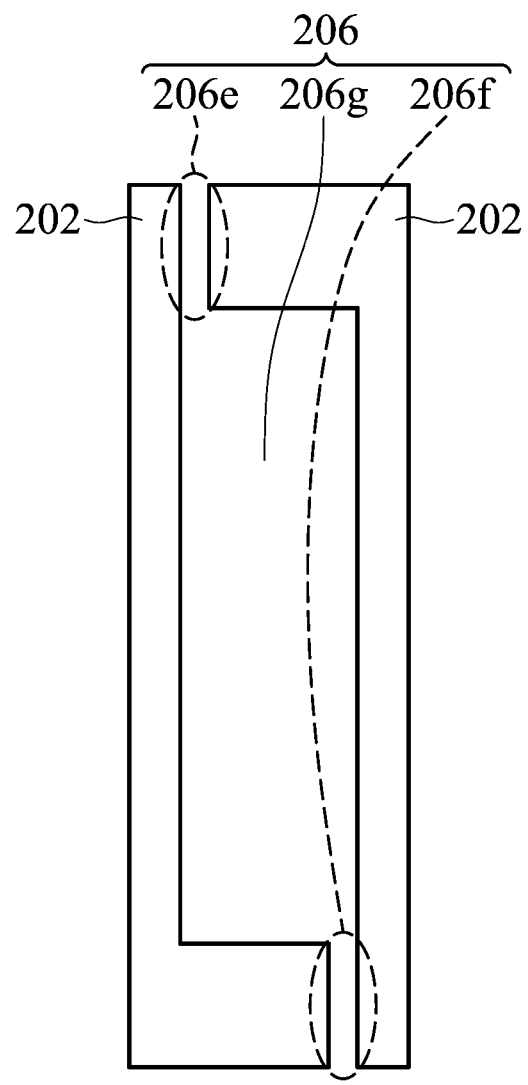

FIG. 6a illustrates yet another exemplary cross section of the magnetic separation unit 200 taken along a line A-A' in FIG. 3. Herein, the trench 206 of the first member 202 comprises a separated fifth section 206e and sixth section 206f, and a seventh section 206g is disposed and respectively connected between the fifth section 206e and the sixth section 206f, thereby forming the fluid channel passing through the first member 202 from a top toward a bottom of the first member 202. The fifth section 206e and the sixth section 206f are illustrated as portions of the trench 206 which are perpendicular to a shorter side of the first member 202, and the fifth section 206e is disposed at a top portion of the first member to function as an input end for receiving a bio-sample solution, and the sixth section 206f is disposed at a bottom portion of the first member 202 to function as an output end for exhausting the bio-sample solution, and the seventh section 206g is illustrated as an inner chamber disposed in the first member 202.

Figure 4B:
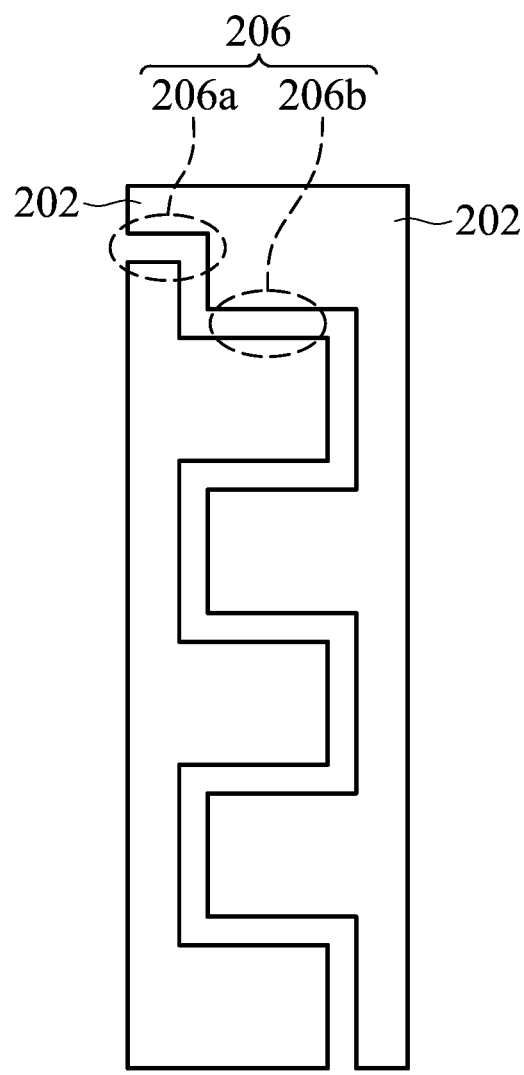
Figure 4C:
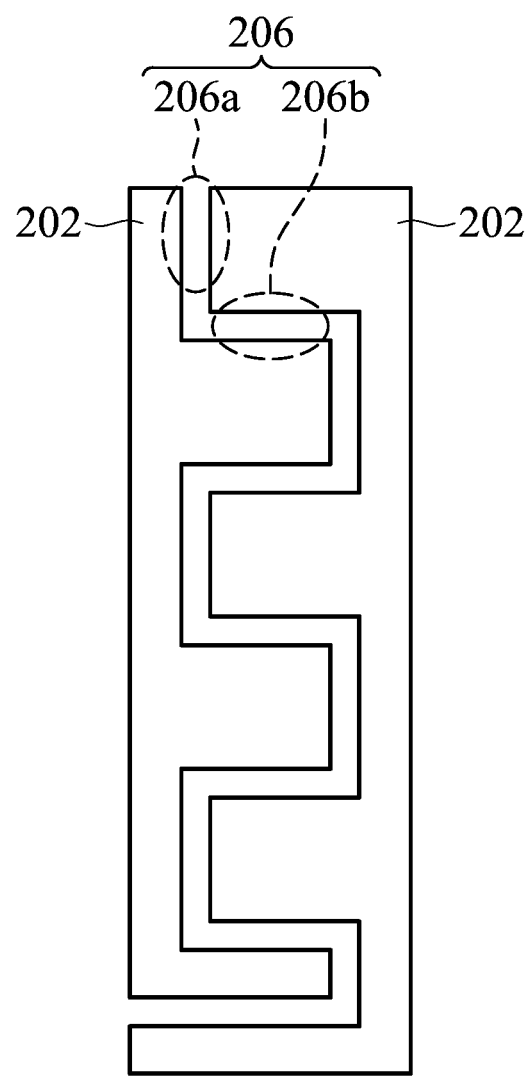
Figure 5B:
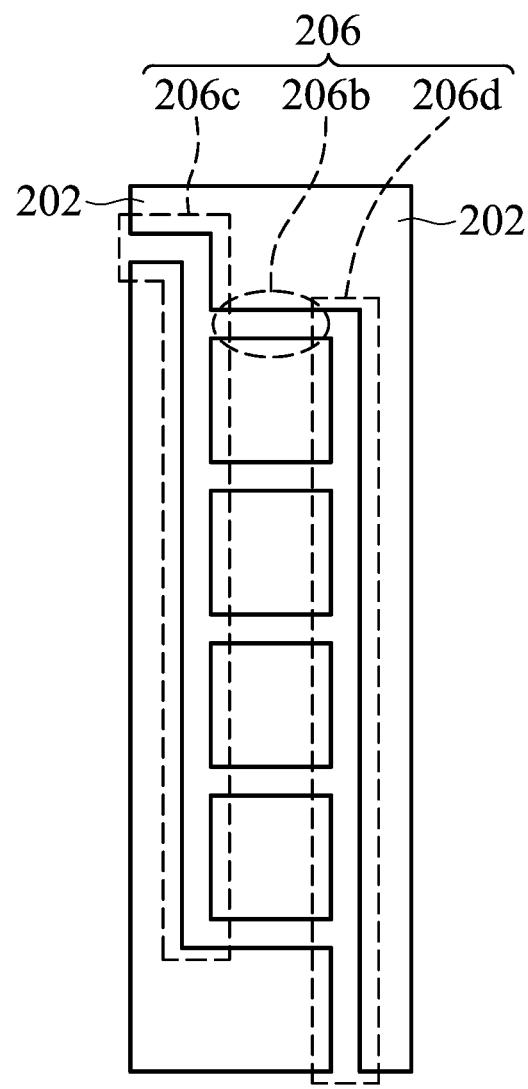
Figure 5C:
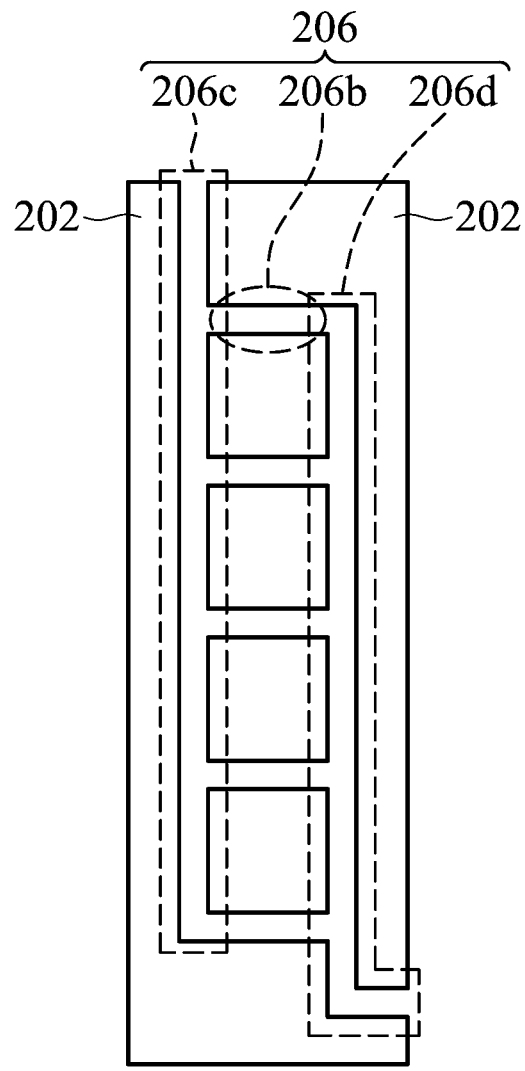
Figure 6B:
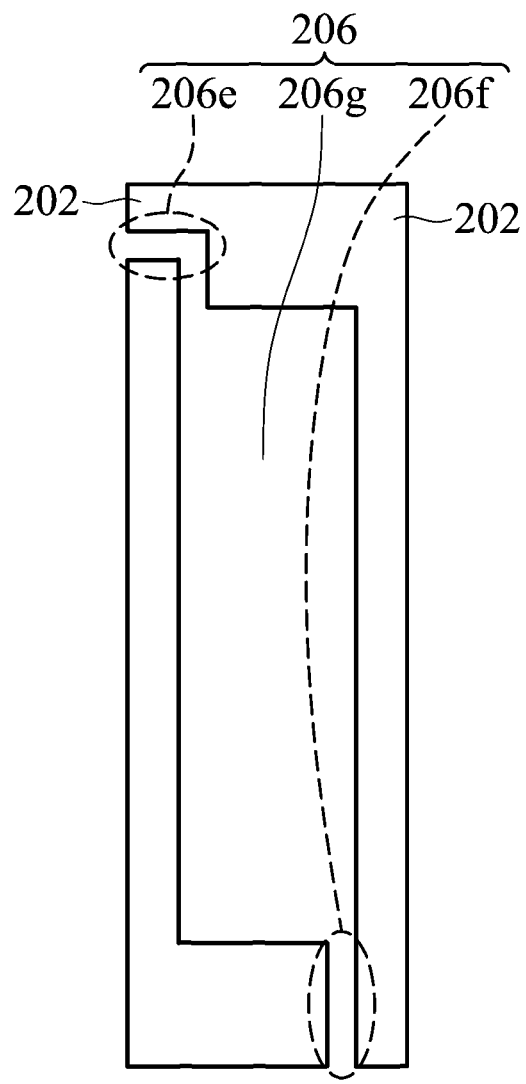
Figure 6C:
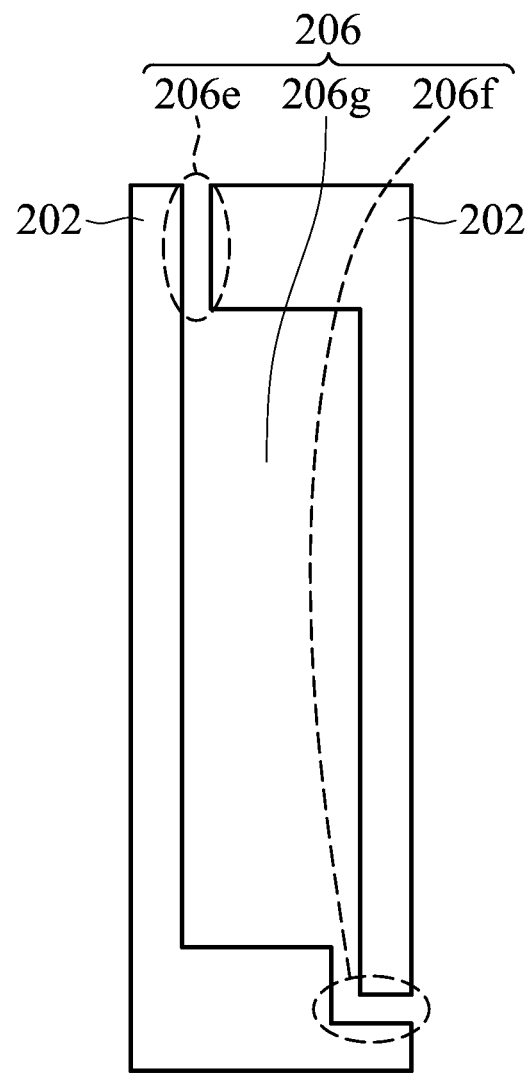

In the embodiments shown in FIGS. 4a, 5a, and 6a, the first section 206a, the third section 206c, the fourth section 206d, the fifth section 206e and the sixth section 206f in each first member 202 are illustrated as a portion of the trench which is perpendicular to a shorter side of the first member 202, and the first section 206a, the third section 206c and the fifth section 206e in the top portion of the first member 202 may function as an input end, and the first section 206a, the fourth section 206d and the sixth section 206f in the bottom portion of the first member 202 may function as an output end, but are not limited thereto. In other embodiments, a portion of the first section 206a, the third section 206c, the fourth section 206d, the fifth section 206e and the sixth section 206f can be disposed at a portion of the longer side of the first member 202. As shown in FIG. 4b, a portion of the topmost first section 206a turns toward a longer side of the first member 202, and as shown in FIGS. 5b and 6b, a portion of the third section 206c and a portion of the fifth section 206e may turn toward a longer side of the first member 202. In addition, as shown in FIGS. 4c, 5c and 6c, a portion of the bottommost first section 206a, a portion of the fourth section 206d, and a portion of the sixth section 206f may respectively turn towards a longer side of the first member 202. Thus, the portions of the sections functioning as input and output ends may face to either a longer side or a shorter side of the first member 202.

Figure 7:
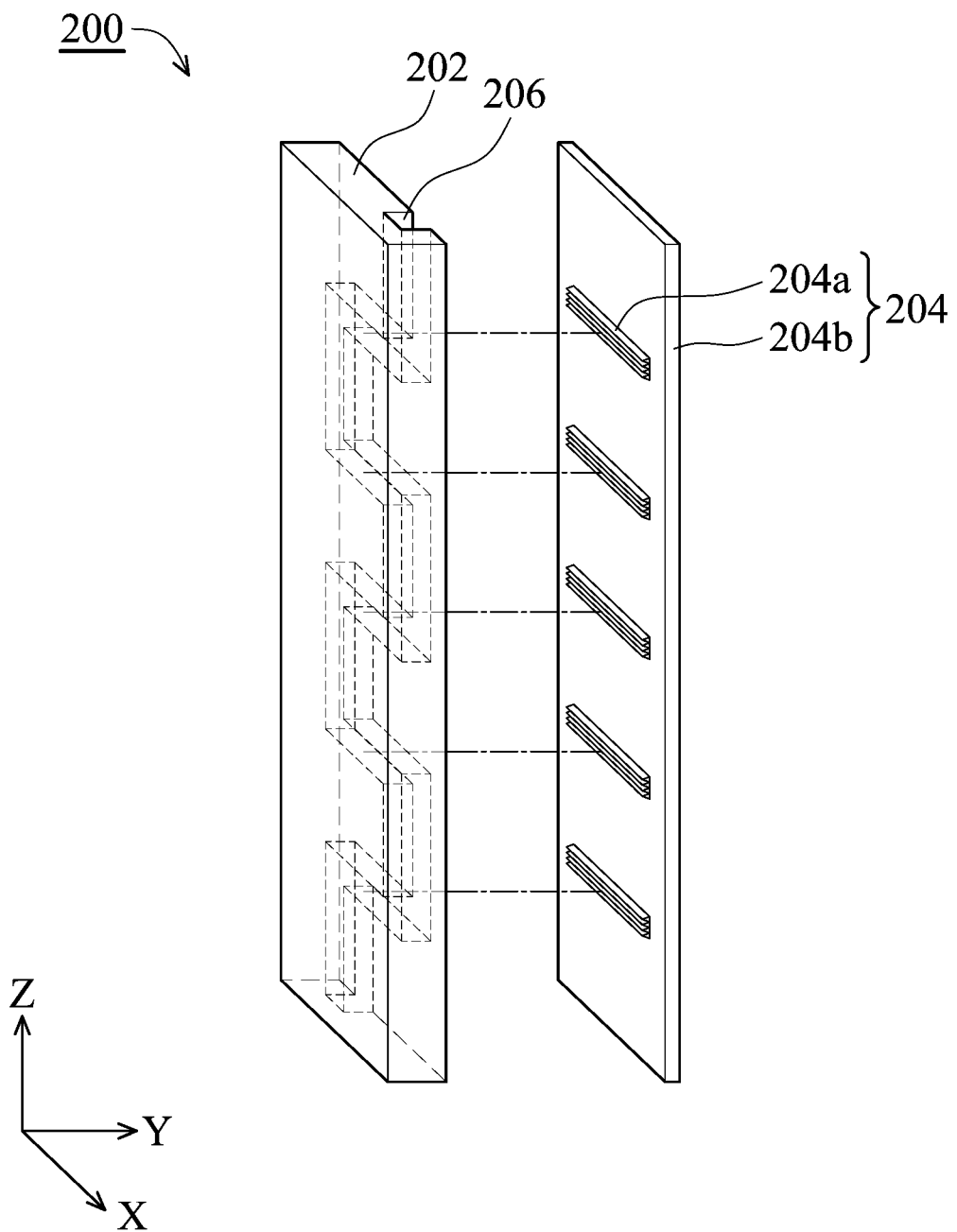
FIG. 7 is an exploded diagram showing components of a magnetic separation unit according to an embodiment of the disclosure.

FIG. 7 is an exploded diagram showing the magnetic separation unit 200, as shown in FIG. 3. Herein, the second member 204 mainly comprises a planar portion 204b and a plurality of protrusion portions 204a, and the protrusion portions 204a are formed over a surface of the planar portion 204b and are opposite to the second sections 206b (see FIGS. 4-5) and the seventh section 206g (see FIG. 6) of the first member 202 and can be contained by the second sections 206b and the seventh section 206g of the first member 202. Numbers and locations of the protrusion portions 204a can be properly adjusted according to the configuration of the first member 202 shown in FIGS. 4-6 and is not limited by that illustrated in FIG. 7.

Figure 8:
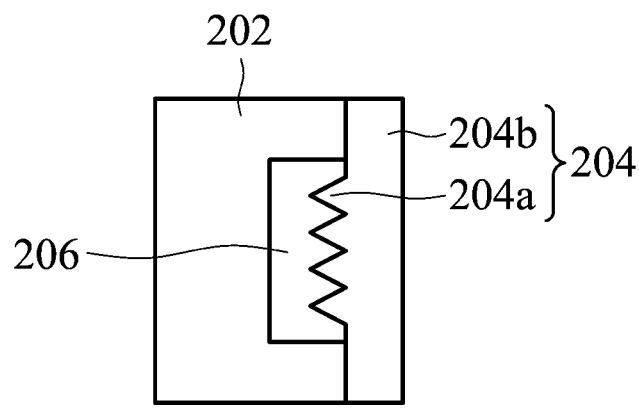
FIGS. 8-9 are schematic diagrams respectively showing a cross sectional view of a region 900 in FIG. 3 according to various embodiments of the disclosure.

FIG. 8 illustrates a cross sectional view of a region 900 as shown in FIG. 3. As shown in FIG. 8, after combination of the first member 202 and the second member 204, a fluid channel is defined by the trench 206 in the first member 202 and the protrusion 204a of the second member 204 is contained by a portion of the fluid channel but not entirely. Due to formation of the second member 204 and the protrusion portions 204a formed thereover, an external magnetic field can be guided to the fluid channel in the magnetic separation unit to enhance the strength of the magnetic field applied to the fluid channel and to increase magnetic separation efficiency.

Figure 9:
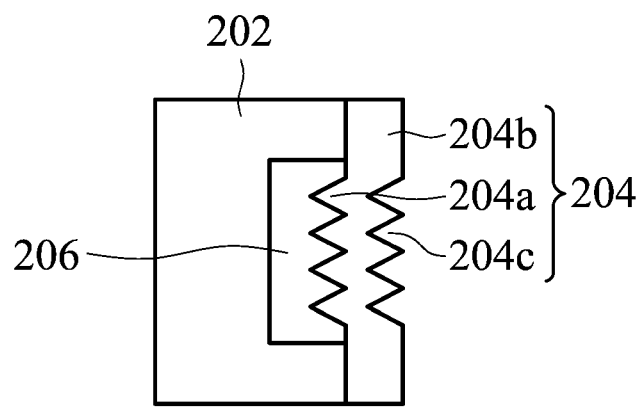

In FIG. 9, another embodiment similar to that shown in FIG. 8 is illustrated. As shown in FIG. 9, another surface opposite to where the protrusion portions 204a are formed is correspondingly formed with a recess portion 204c such that an external magnetic field can be further guided to the fluid channel in the magnetic separation unit to enhance the strength of the magnetic field applied to the fluid channel and to increase magnetic separation efficiency.

As shown in FIGS. 8-9, the protrusion portions 204a and the recess portions 204c are illustrated as successive triangle-shaped protrusions but are not limited thereto. The portions can be successive protrusions with other shapes such as rectangular, trapezoid or curve shapes.

In the magnetic separation unit shown in FIGS. 3-9, the first member 202 is made of non-magnetic materials such as plastic, bakelite, non-magnetic metal or ceramic and is not limited thereto, and the trench 206 can be formed therein by suitable processing methods. The second member 204 is made of magnetic materials such as pure iron, magnetic stainless steel, metal soft magnetic materials of predetermined permeability, or soft magnetic ferrites. The metal soft magnetic materials of predetermined permeability can be, for example, iron, silicon steel, NiFe, CoFe, stainless steel, soft magnetic ferrites, or combinations thereof.

FIGS. 10-15 illustrate magnetic separation devices according to various embodiments of the disclosure, wherein each of the magnetic separation devices may incorporate the magnetic field units and the magnetic separation units described and illustrated previously.

Figure 10:
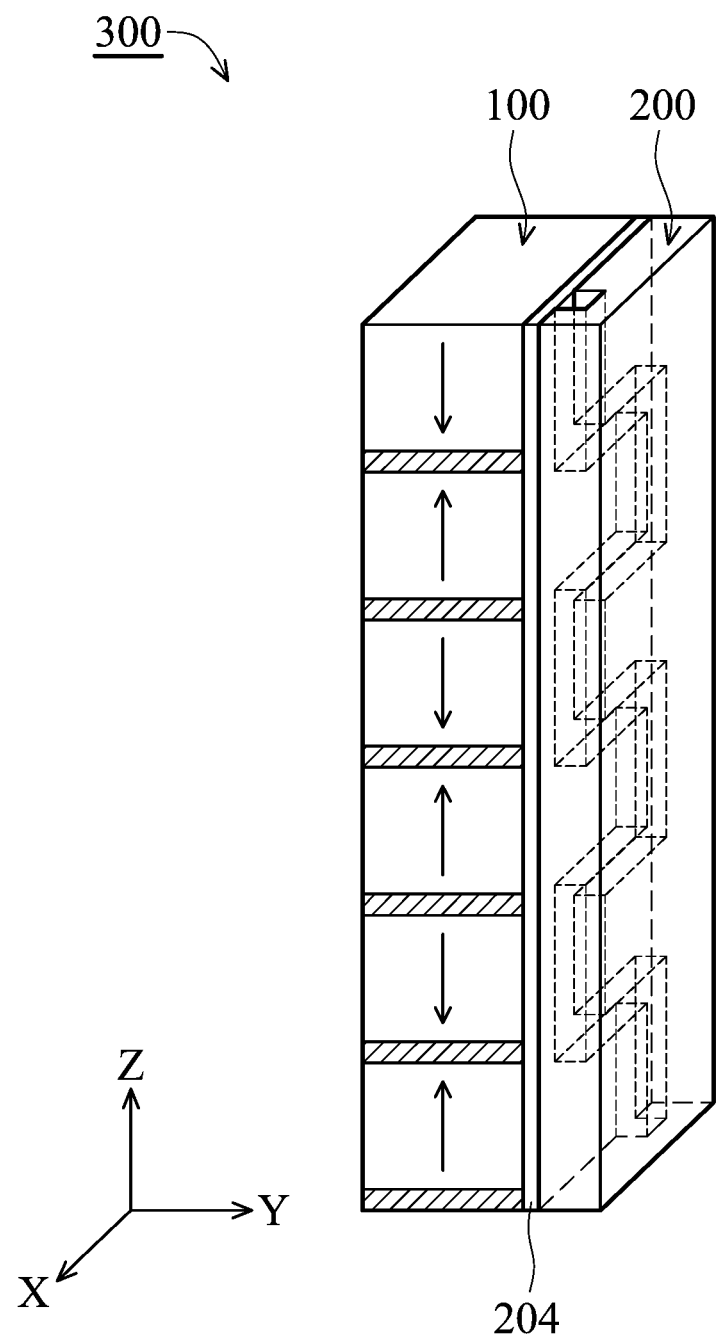
FIGS. 10-15 are schematic diagrams showing a magnetic separation device according to various embodiments of the disclosure.

FIG. 10 illustrates an exemplary magnetic separation device 300 comprising the magnetic field unit 100, as shown in FIG. 1 and the magnetic separation unit 200, as shown in FIG. 3. Herein, the magnetic separation unit 200 is disposed at a side of the magnetic field unit 100 by methods such as hooking or adhering, and the second member 204 in the magnetic separation unit 200 is preferably adjacent to the magnetic field unit 100, and a portion of the second sections 206b shown in FIGS. 4-5 or the seventh section 206g shown in FIG. 6 is parallel to a side of each of the magnetic yokes 104 in the magnetic field unit 100. In such a configuration as shown in FIG. 10, magnetic flux lines (not shown) of two magnets adjacent to one of the magnetic yokes 104 in the magnetic field unit 100 are gathered to the magnetic yoke 104 interposed therebetween, and the magnetic flux lines are further guided to the second sections 206b (see FIGS. 4-5) or the seventh section 206g (see FIG. 6) of the trench 206 in the magnetic separation unit 200 adjacent and parallel to the magnetic yoke 104 by the protrusion portions 204a of the second member 204 of the separation unit 200, thereby making the second sections 206b shown in FIGS. 4-5 or the seventh section 206g shown in FIG. 6 of the trench 206 of the magnetic separation unit 200 as the main separation portions in the magnetic separation device 300 for separating magnetic substances in a bio-sample solution. In one embodiment, the main separation sections have a depth D of about 0.1-2 mm.

Figure 11:
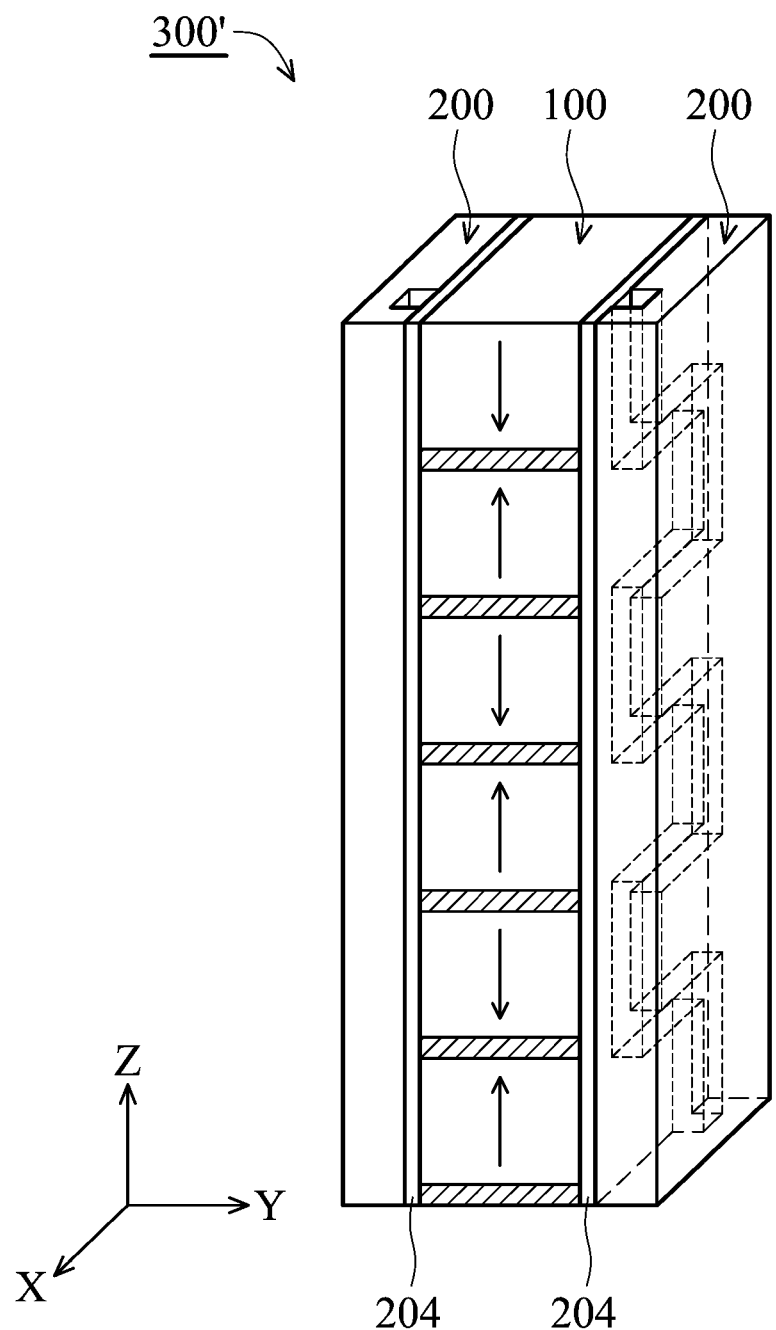

FIG. 11 illustrates another exemplary magnetic separation device 300' similar to the magnetic separation device 300 illustrated in FIG. 10. Herein, the same references represent the same components, and only differences therebetween are discussed in the following paragraphs.

As shown in FIG. 11, the magnetic separation device 300' comprises a magnetic field unit 100, as shown in FIG. 1 and two magnetic separation units 200, as shown in FIG. 3. The magnetic separation units 200 are disposed on opposite sides of the magnetic field unit 100, respectively, and the second member 204 of each of the magnetic separation units 200 is preferably adjacent to the magnetic field unit 100. Through such a configuration, as shown in FIG. 11, the magnetic separation device 300' may provide a magnetic separation process for simultaneously separating more than one set of solutions of bio-samples, thereby improving throughput and efficiencies of the magnetic separation process.

In other embodiments, configurations of the magnetic separation unit 200 in the magnetic separation device are not limited to those illustrated in FIGS. 10-11. A magnetic separation unit may be provided at each side of the magnetic field unit, or the magnetic separations units 200 can be located at adjacent sides of the magnetic field unit to improve throughput and efficiencies of the magnetic separation process.

Figure 12:
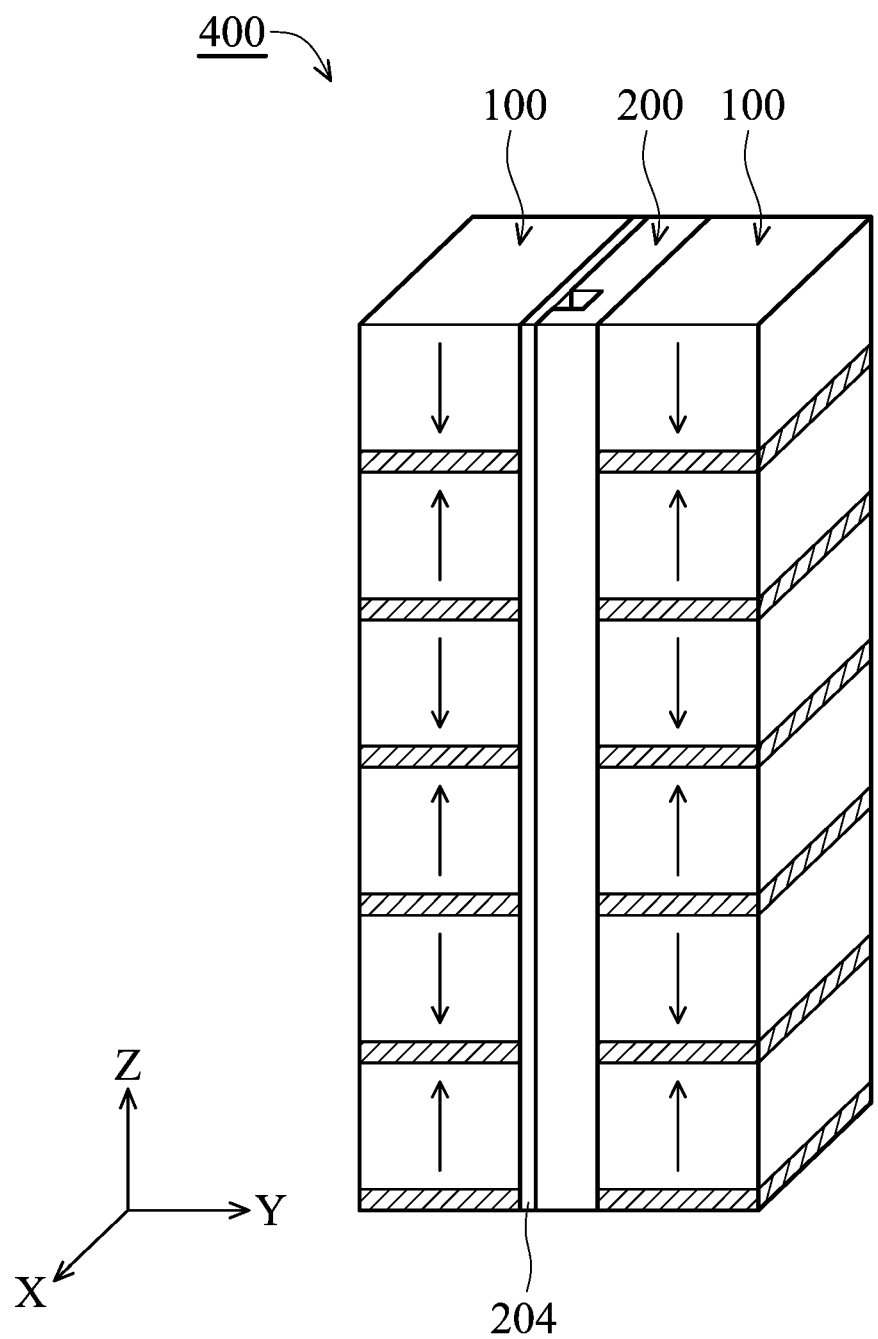

FIG. 12 illustrates another exemplary magnetic separation device 400, comprising two magnetic field units 100, as shown in FIG. 1 and a magnetic separation unit 200, as shown in FIG. 3. Herein the magnetic separation unit 200 is interposed between the magnetic field units 100, and the magnetic separation unit 200 can be disposed at a side of each of the magnetic field units 100 by methods such as hooking or adhering, and the second member 204 in the magnetic separation units 200 is adjacent to one of the magnetic field units 100, and portions of the second sections 206b shown in FIGS. 4-5 or the seventh section 206g shown in FIG. 6 of the trench 206, adjacent and parallel to a side of each of the magnetic yokes 104 in the magnetic field unit 100. For such a configuration, as shown in FIG. 12, magnetic flux lines (not shown) of two magnets adjacent to one of the magnetic yokes 104 in the magnetic field unit 100 are gathered to the magnetic yoke 104 interposed therebetween, and the magnetic flux lines are further guided to the second sections 206b (see FIGS. 4-5) or the seventh section 206g (see FIG. 6) of the trench 206 in the magnetic separation unit 200 adjacent and parallel to the magnetic yoke 104 by the protrusion portions 204a of the second member 204 of the separation unit 200, thereby making the second sections 206b shown in FIGS. 4-5 or the seventh section 206g shown in FIG. 6 of the trench 206 of the magnetic separation unit 200 as main separation portions in the magnetic separation device 400 for separating magnetic substances in a bio-sample solution. In addition, more than one set of the magnetic field units can be disposed in the magnetic separation device 400 to further improve magnetic field strength such that the efficiency of magnetic separation can be improved.

Figure 13:
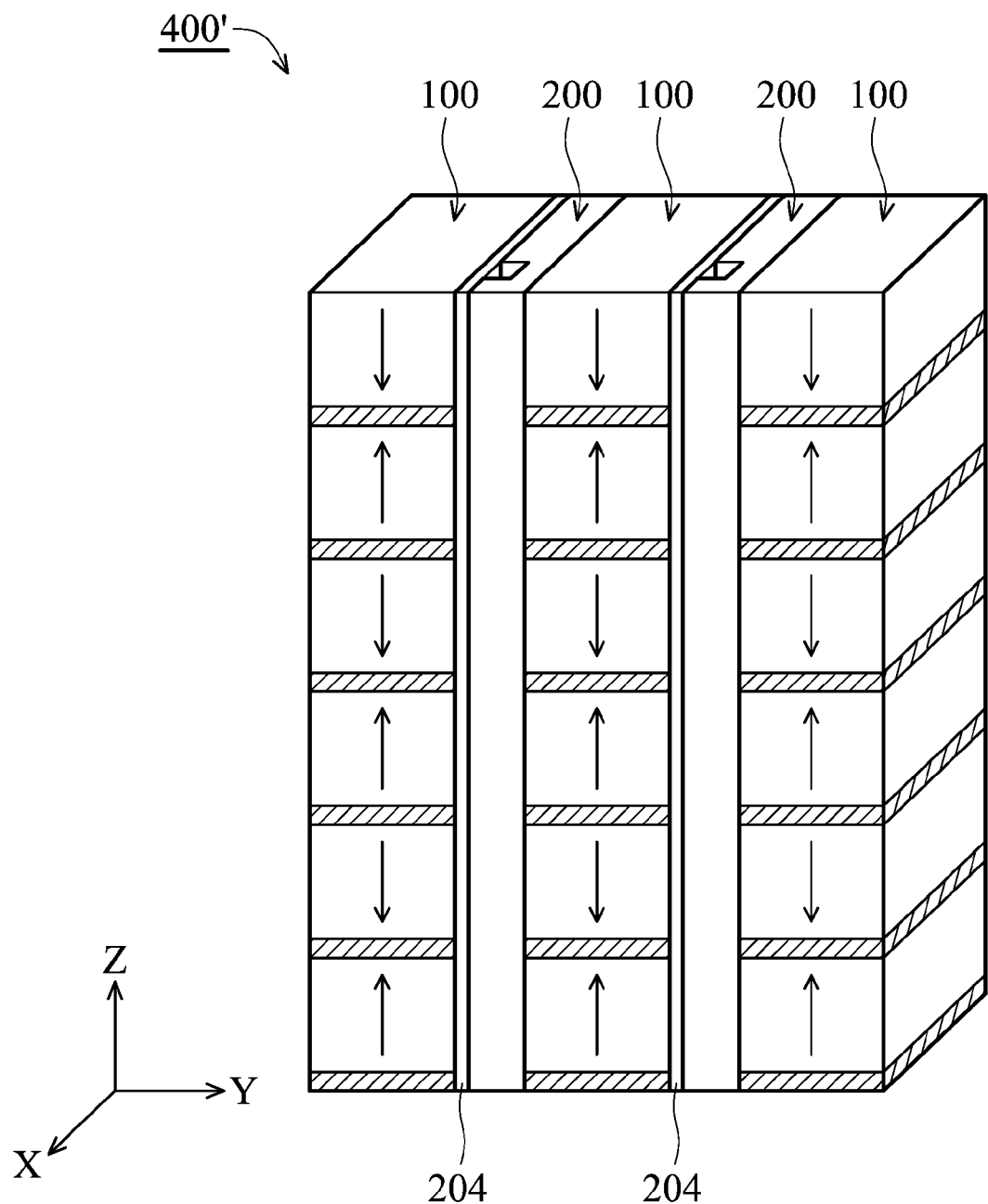
Figure 14:
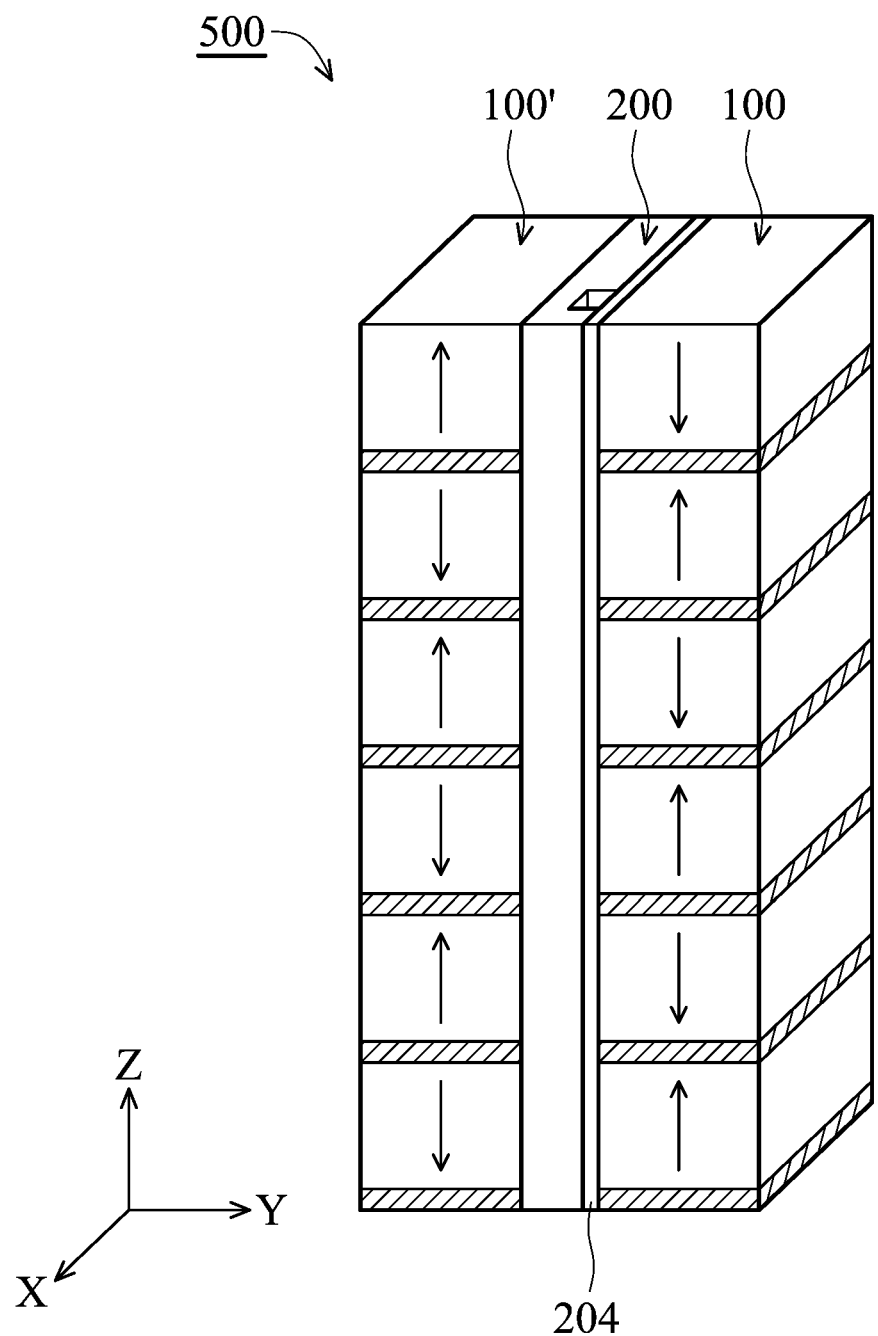
Figure 15:
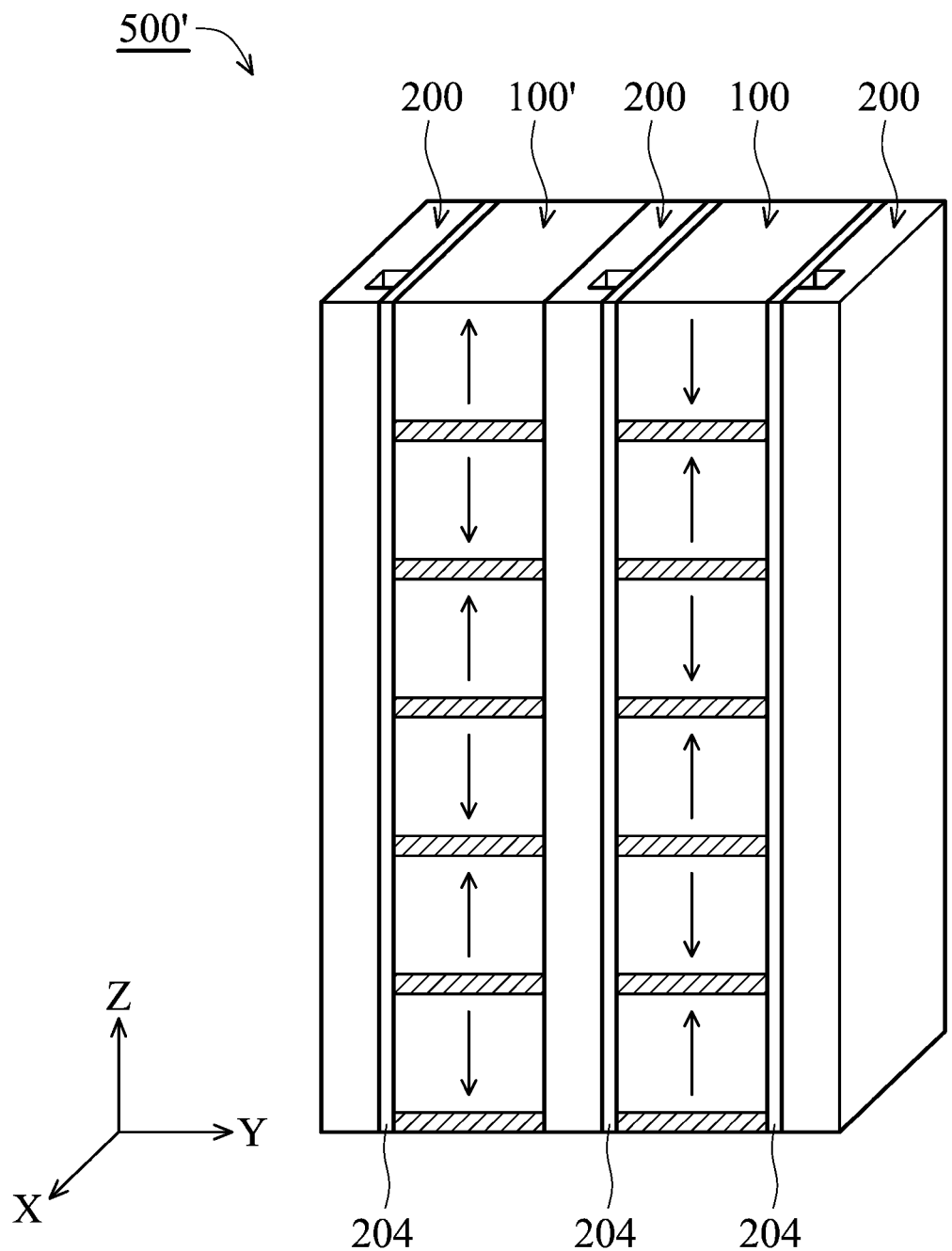

In other embodiments, the numbers and configurations of the magnetic separation units 200 and the magnetic field units 100 disposed in the magnetic separation device are not limited to those illustrated in FIG. 12. As shown in FIG. 13, a magnetic separation unit can be respectively interposed between a number of n (n is an integer greater than 2 and n=3 in this embodiment) magnetic field units such that the magnetic separation device provides a magnetic separation device 400' comprising n magnetic field units and n−1 magnetic separation units. FIG. 14 illustrates another exemplary magnetic separation device 500 formed by replacing one of the magnetic field units 100 therein with the magnetic field unit 100' shown in FIG. 2. FIG. 15 illustrates an exemplary magnetic separation device 500' formed by replacing one of the n magnetic field units 100 with the magnetic field unit 100' illustrated in FIG. 2. The previously illustrated configurations of the magnetic separation device are good for improving efficiency of the magnetic separation process provided thereby. In the embodiments shown in FIGS. 14-15, the second member 204 of each magnetic separation unit 200 is preferably adjacent to the magnetic field unit 100 and 100', and the second member 204 of each magnetic separation unit 200 disposed between the magnetic field unit 100 and 100' is adjacent to the magnetic field unit 100 or 100'

Figure 16:
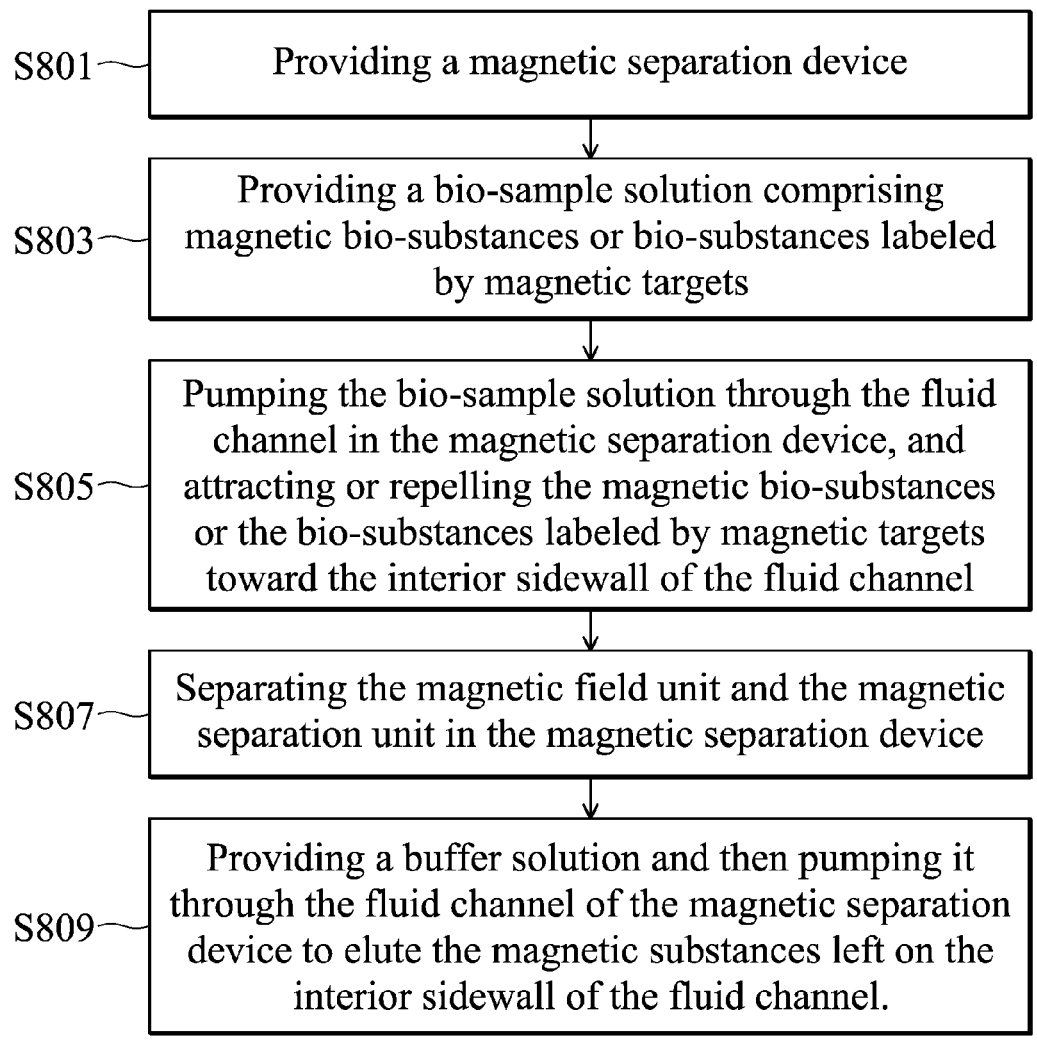
FIG. 16 is a flow chart showing a method for separating magnetic substances in bio-samples according to an embodiment of the disclosure.

FIG. 16 illustrates a flow chart of a method for separating magnetic substances in bio-samples.

First, in step S801, a magnetic separation device such as one of the magnetic separation devices illustrated in FIGS. 10-15 is provided. Next, in step S803, a bio-sample solution comprising magnetic substances is provided. The magnetic substances can be magnetic bio-substances or bio-substances labeled with magnetic targets. Next, in step 805, the bio-sample solution is then pumped through the fluid channel in the magnetic separation device and the magnetic substances therein are attracted or repelled toward the interior sidewalls of the fluid channel, such as toward the interior sidewalls of the second section or the seventh section near the magnetic yoke and portions of the interior sidewalls adjacent to the magnetic yoke. Next, in step S807, the magnetic field unit and the magnetic separation unit in the magnetic separation device are separated by individually removing the magnetic separation unit or the magnetic field unit. In one embodiment, the magnetic separation unit is removed from the magnetic separation device. Finally, in step S809, a buffer solution is provided and then flowed through the fluid channel of the magnetic separation device to elute the magnetic substances left on the interior sidewalls of the second section or the seventh section of the fluid channel and other sections adjacent thereto.

In one embodiment, the solution of the bio-sample may flow through magnetic separation device and may comprise magnetic substances or bio-substances labeled by magnetic targets. The bio-sample can be, for example, blood samples, condensed blood samples, tissue samples, tissue solution samples, cell samples, cell culture samples, microorganism samples, protein samples, amino acid samples, and nucleic acid samples. The magnetic substances can be, for example, metal particles such as Fe, Co, Ni, or oxide particles thereof. The buffer solution can be, for example, Tris-buffer saline (TBS), phosphate buffer saline (PBS), normal saline, and solutions having the same tension as a culture solution and other solutions capable of maintaining activities of proteins, amino acids or nucleic acids.

Example 1

A magnetic separation device as illustrated in FIG. 10 was provided, comprising magnets 102 made of NdFeB and an overall size (length×width×height) of 40 mm×40 mm×40 mm. The magnetic yokes 104 were made of pure iron and was formed with an overall rectangular size (length×width) of 40 mm×40 mm and a thickness of about 2.4 mm. The first member 202 in the magnetic separation unit 200 has a trench 206 with an overall size (length×width×height) of 25 mm×145 mm×200 μm formed by processing acrylic materials and the inlet and outlet for the sample flow in and out were formed in the first member 202 by drilling. The second member 204 in the magnetic separation unit 200 was made of permalloy and has a thickness of about 0.1 mm, having protrusions 204a of a protrusion dimension of about 0.1 mm, wherein the protrusion 204a of the second member 204 was disposed depending on the strong magnetic regions in the magnetic separation unit. A bio-sample was pumped through the fluid channel in the magnetic separation unit, wherein the bio-sample was a solution comprising $Fe_3O_4$ particles with a size of 30 nm-1000 nm therein. The Fe contents in the solutions before and after separation were measured. Table 1 shows the measurement results and separation efficiency of the bio-sample 1 was 94.9%.

TABLE 1

| Before separation | 0.2685 mg/g |
|---|---|
| After separation | 0.0136 mg/g |
| Separation efficiency | 94.9% |

Example 2

Separation efficiency tests were performed by using the magnetic separation device disclosed in example 1. The test samples were commercial BD IMag magnetic particles with particle sizes of about 100-450 nm. A wash solution was collected when the test sample flowed through the magnetic separation device. Then the magnetic separation unit was removed, and the elution was collected when a buffer solution is pumped through the fluid channel. Fe contents in the wash and elution was measured. Table 2 shows the measurement results and separation efficiency of the bio-sample 2 was 98.4%.

TABLE 2

| Wash | 14.23 μg |
|---|---|
| Elution | 856.5 μg |
| Separation efficiency | 98.4% |

While the disclosure has been described by way of examples and in terms of several embodiments, it is to be understood that the disclosure is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A magnetic separation unit, comprising:
a first member made of non-magnetic materials, comprising a trench extending within the first member; and
a second member, comprising a planar portion and a protrusion portion protruding over a surface of the planar portion, wherein both the planar portion and the protrusion portion are made of magnetic materials, and wherein the first member is connected to the planar portion of the second member to form a fluid channel between the first member and second member, and the protrusion portion of the second member protrudes into the trench of the first member.

2. The magnetic separation unit as claimed in claim 1, wherein the first member comprises plastic, bakelite, non-magnetic metal or ceramic.

3. The magnetic separation unit as claimed in claim 1, wherein the second member comprises pure iron, magnetic stainless steel, metal soft magnetic materials of predetermined permeability, or soft magnetic ferrites.

4. The magnetic separation unit as claimed in claim 1, wherein the trench comprises a plurality of first sections and a plurality of second sections, and the first sections are substantially perpendicular to the second sections, and the first sections respectively connect to one of the second sections to form the fluid channel.

5. The magnetic separation unit as claimed in claim 1, wherein the trench comprises separated first and second sections and a plurality of third sections, and the third sections are simultaneously disposed and connected between the first and second sections to form the fluid channel, and the first section is parallel to the second section.

6. The magnetic separation unit as claimed in claim 5, wherein the first and second sections are substantially perpendicular to the third sections.

7. The magnetic separation unit as claimed in claim 1, wherein the trench comprises separated first and second sections, and a third section is formed between the first and second sections simultaneously connecting to the first and second sections to form the fluid channel, and the third section is an inner chamber disposed in the first member.

8. The magnetic separation unit as claimed in claim 7, wherein the first and second sections are parallel or perpendicular to each other.

9. The magnetic separation unit as claimed in claim 1, further comprising a recess portion disposed on another surface of the second member opposite to the surface of the second member with the protrusion portion.

10. The magnetic separation unit as claimed in claim 9, wherein the protrusion portion and the recess portion of the second member comprise successive protrusions.

11. A magnetic separation device, comprising:
 a first magnetic field unit, comprising:
  a first magnetic yoke having opposite first and second surfaces; and
  a plurality of first magnets respectively disposed over the first and second surfaces, wherein the same magnetic poles of the plurality of first magnets face the first magnetic yoke; and
 the magnetic separation unit as claimed in claim 1 disposed at one side of the first magnetic field unit, wherein the second member of the magnetic separation unit is adjacent to the first magnetic field unit.

12. The magnetic separation device as claimed in claim 11, wherein the first magnetic yoke comprises pure iron, magnetic stainless steel, metal soft magnetic materials of predetermined permeability, or soft magnetic ferrites.

13. The magnetic separation device as claimed in claim 11, wherein the first magnets comprise NdFeB, SmCo, SmFeN, AlNiCo, or ferrite.

14. The magnetic separation device as claimed in claim 11, further comprising a plurality of magnetic separation units disposed on different sides of the first magnetic field unit, respectively, wherein the second member in the magnetic separation units is adjacent to the first magnetic field unit.

15. The magnetic separation device as claimed in claim 14, wherein the magnetic separation units are disposed at adjacent sides or opposite sides of the first magnetic field unit.

16. The magnetic separation device as claimed in claim 11, further comprising a second magnetic field unit, comprising:
 a second magnetic yoke having opposite first and second surfaces; and
 a plurality of second magnets, respectively disposed over the first and second surfaces of the second magnetic yoke, wherein the same magnetic poles of the second magnets face the second magnetic yoke, wherein the magnetic separation unit is also disposed at a side of the second magnetic field unit, and the first member of the magnetic separation unit is adjacent to the second magnetic field unit.

17. The magnetic separation device as claimed in claim 16, wherein the second magnetic field unit and the first magnetic field unit are disposed at opposite sides of the magnetic separation unit, and a magnetic direction of the second magnets is the same as or opposite to a magnetic direction of the first magnets adjacent thereto.

18. The magnetic separation device as claimed in claim 16, wherein the second magnetic yoke comprises pure iron, magnetic stainless steel, soft metal magnetic materials having predetermined permeability, or soft magnetic ferrites.

19. The magnetic separation device as claimed in claim 16, wherein the second magnets comprise NdFeB, SmCo, SmFeN, AlNiCo, or ferrite.

20. A method for separating magnetic substances in a bio-sample, comprising:
 providing a magnetic separation device as claimed in claim 11;
 providing a bio-sample solution, wherein the bio-sample solution comprises magnetic bio-substances or bio-substances labeled by a magnetic target;
 pumping the bio-sample solution through the fluid channel in the magnetic separation device, thereby attracting or repelling the magnetic bio-substances or bio-substances labeled by a magnetic target toward a sidewall of the magnetic separation unit adjacent and parallel to the first magnetic yoke;
 separating the first magnetic field unit from the magnetic separation unit; and
 providing a buffer solution and pumping the buffer solution through the fluid channel of the magnetic separation device, thereby eluting the magnetic bio-substances or bio-substances labeled by magnetic targets left on the sidewall of the magnetic separation unit.

21. The method as claimed in claim 20, wherein the magnetic bio-substances or the bio-substances labeled by the magnetic target in the bio-sample solution are cells, microorganisms, proteins, amino acids, nucleic acids.

22. The method as claimed in claim 20, wherein the magnetic targets are particles of iron, cobalt, nickel, or oxides thereof.

23. The method as claimed in claim 20, wherein the buffer solution comprises Tris-buffer saline, phosphate buffer saline, normal saline, solutions having same tension as a culture solution, or solutions capable of maintaining activities of proteins, amino acids or nucleic acids.

* * * * *